US00PP33844P2

(12) United States Plant Patent
Hansen

(10) Patent No.: US PP33,844 P2
(45) Date of Patent: Jan. 11, 2022

(54) ***BUDDLEIA* PLANT NAMED 'LILAC CASCADE'**

(50) Latin Name: *Buddleia davidii*
Varietal Denomination: Lilac Cascade

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,647

(22) Filed: Sep. 8, 2021

(51) Int. Cl.
*A01H 5/00* (2018.01)
*A01H 6/00* (2018.01)

(52) U.S. Cl.
USPC ..... Plt./242

(58) Field of Classification Search
USPC ..... Plt./226, 242
See application file for complete search history.

*Primary Examiner* — Susan McCormick Ewoldt
*Assistant Examiner* — Karen M Redden

(57) ABSTRACT

The new and distinct plant of *Buddleia* 'Lilac Cascade' is a rounded-mounded, multi-stemmed, winter-hardy butterfly bush with very long, narrow, outwardly drooping flowering thyrse producing a waterfall effect over a long season beginning mid-summer with sweetly-fragrant flowers of pale lilac petals that are attractively offset by dark green foliage with silvery undersides. No seed has been observed since development. The new plant is valuable for landscaping en masse, as an accent or as a potted specimen.

1 Drawing Sheet

Botanical classification: *Buddleia davidii.*
Variety denomination: 'Lilac Cascade'.

STATEMENT REGARDING PRIOR DISCLOSURES UNDER 37 CFR 1.77(B)(6)

The first public disclosure of the claimed plant, in the form of a sale, was made by Walters Gardens, Inc. on Sep. 21, 2020 to both Plant Delights Nursery and Burpee Co. Prior to that, on Feb. 1, 2020 the claimed plant was displayed with a non-enabling photograph and brief description in a website operated by Walters Gardens, Inc., and on May 21, 2020 as a non-enabling photograph and brief description in the 2020-2021 Catalog by Walters Gardens, Inc., who obtained the plant and all information relating thereto, from the inventor. No plants of *Buddleia* 'Lilac Cascade' were in condition to sell prior to the first sale date, nor have been sold, in this country or anywhere in the world, nor has any disclosure of the new plant been made more than one year prior the filing date of this application, and such sale or disclosure within one year was either derived directly or indirectly from the inventor.

BACKGROUND OF THE PLANT

The present invention relates to the new and distinct butterfly bush plant of the Scrophulariaceae family, *Buddleia* 'Lilac Cascade' hybridized by Hans A. Hansen on Aug. 15, 2015 at a wholesale perennial nursery in Zeeland, Mich., USA. 'Lilac Cascade' is the result of an ongoing breeding program conducted by the inventor. The goals for this program have been to produce improved, garden-worthy plants for the ornamental plant market. The new plant, assigned the breeder code 15-43-102 toward the end of the evaluation trials was the result of a single seedling selection from a cross between the unreleased proprietary hybrid known by the breeder code 14-18-2 (not patented) as the female or seed parent. The male parent was the unreleased proprietary hybrid named by the breeder code 14-38-2 (not patented). The new cultivar was selected as single individual flowering plant within the progeny of the above cross at the same nursery in Zeeland, Mich.

No plants of *Buddleia* 'Lilac Cascade' have been sold, under this or any other name, in this country or anywhere in the world, prior to the filing of this application, nor has any disclosure of the new plant been made prior to the filing of this application with the exception of that which may have been sold or disclosed within one year of the filing date of this application and was either derived directly or indirectly from the inventor.

*Buddleia* 'Lilac Cascade' was first asexually propagated from a single select plant in 2017 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

In comparison to the new plant, the female parent has a taller habit with darker flowers and less drooping and broader more spreading thyrse. The male flower has longer narrower and more drooping or arching thyrse with similar flower color. Both parents were fertile.

The nearest comparison plants known to the inventor are: 'Wisteria Lane' U.S. Plant Pat. No. 27,833, 'Grand Cascade' U.S. Plant Pat. No. 30,868, 'Lavender Cascade' U.S. Plant Pat. No. 30,635, 'Glass Slippers' U.S. Plant Pat. No. 27,832 'Dartmoor' (not patented). 'Wisteria Lane' is shorter in habit with smaller thyrse, the branches are more drooping instead of mainly the thyrses drooping and the petals are light purple. 'Grand Cascade' is larger in habit and has longer and broader thyrse with petals that are light lavender-purple colored. 'Lavender Cascade' has taller and broader habit and flower petals that are light purple. 'Glass Slippers' has a less drooping thyrse and the flower color is white. 'Dartmoor' has a taller habit, with shorter stockier thyrse of darker flowers.

*Buddleia* 'Lilac Cascade' is a unique winter-hardy butterfly bush different from all other *Buddleia* cultivars known to the inventor based on the following combined repeatedly observed distinguishing traits:

1. Winter-hardy butterfly bush shrub, with multiple-stemmed, well-branched, rounded, waterfall-type arching, mounded habit;
2. Large, narrow, many-flowered, elongated and outwardly-drooping thyrse flowering over a prolonged season beginning mid-summer;
3. Flowers with pale lilac petals;
4. Lanceolate foliage of dark green with silvery undersides;
5. No seed production has been observed since development.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
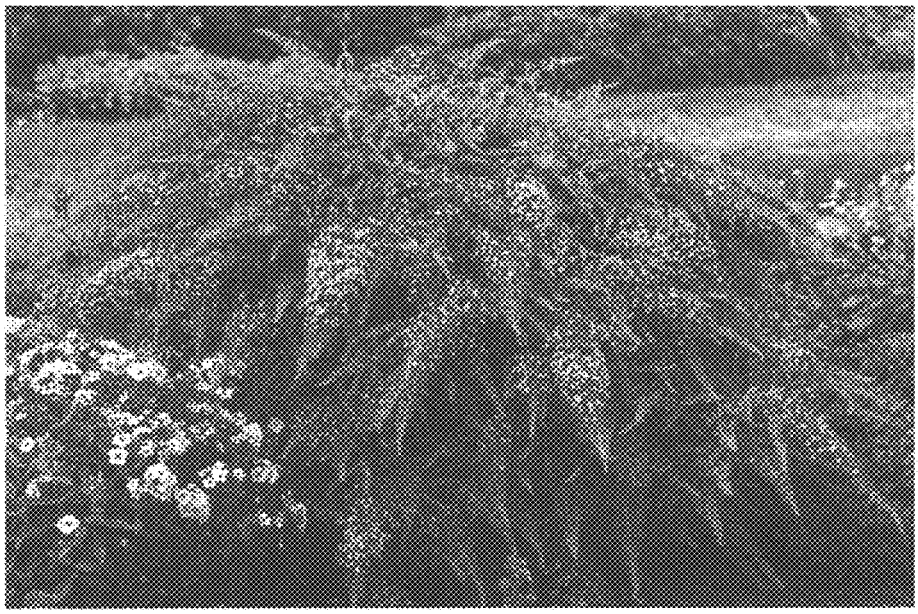
FIG. 1 shows the habit of a four-year-old plant in mid-season flowering.
Figure 2:
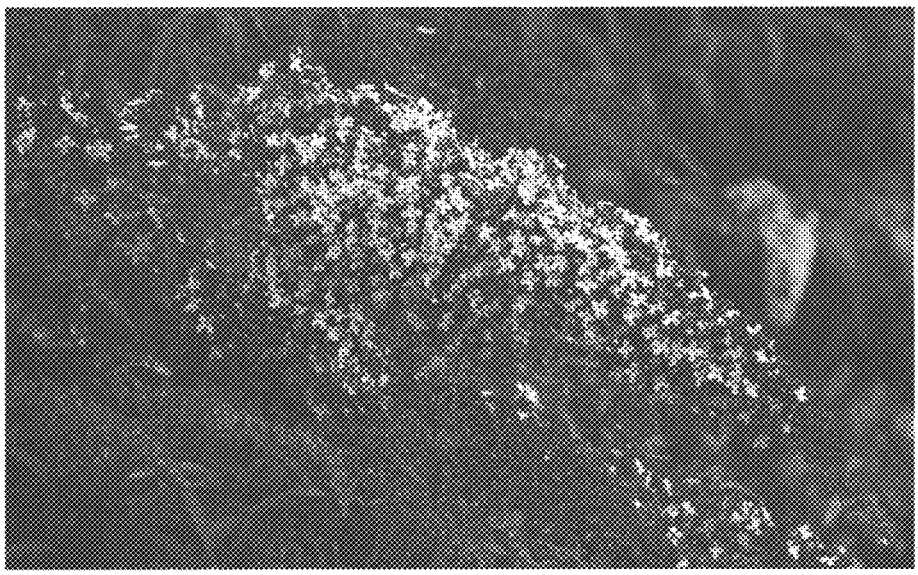
FIG. 2 shows a close-up of the inflorescence.

The following descriptions and color references are based on the 2015 edition of The Royal Horticultural Society Colour Chart except where common dictionary terms are used. The new plant, *Buddleia* 'Lilac Cascade', has not been observed under all possible environments. The phenotype may vary slightly with different environmental conditions, such as temperature, light, fertility, moisture and maturity levels, but without any change in the genotype. The following observations and size descriptions are of four-year-old plants in the loamy-sand, open-sun, display garden of a nursery in Zeeland, Mich. with supplemental fertilizer and water as needed. The plants are natural habit and were not treated with plant growth regulators, nor were they pinched at any time in the growth year except to cut back woody stems to about 15 cm tall in early spring.

Parentage: Unreleased proprietary hybrid 14-18-2 as the female or seed patent; the male or pollen parent was the unreleased, proprietary, hybrid known by 14-38-2;

Propagation:

*Method*.—Softwood shoot cuttings.

*Time to initiate roots from tissue culture*.—About two weeks.

*Rooting habit*.—Normal, dense and branching, developing thick at base to about 1.5 cm diameter.

*Root color*.—Creamy white between RHS 159A and lighter than RHS 159 D depending on soil type.

*Crop time*.—Under normal summer growing conditions 12 to 15 weeks to flower in a four-liter container from cutting. Plant vigor is very good.

Plant description:

*Plant shape and habit*.—Winter-hardy, herbaceous to semi-woody, well-branched shrub with about 17 moderately thick upright and branched main stems producing a rounded mound, to about 138 cm tall and about 228 cm wide.

*Stem*.—Terete and woody in lower portion, with exfoliating bark; younger upper portion tomentose to tomentulose; strong and flexible, arching or drooping especially in terminal thyrse; average about 120 cm long from soil line to just below terminal flowers, and about 15.0 mm diameter at the base; about 34 branches per main stem before distal flowers in upper 28 nodes, extending at about 60° angle from perpendicular main stem.

*Stem color*.—Young distal portion just below flowers nearest RHS 148D; basal 15 cm with striations of nearest RHS 200D and between RHS 199D and RHS 161C.

*Internode*.—About 17 nodes per main stem below terminal thyrse, average internode length about 7.0 cm on unpinched plant; upper internodes slightly more elongated than lower internodes.

Foliage description: Opposite; lanceolate; decussate; serrate with about 3.3 teeth per cm, teeth about 0.5 mm long and 1.0 mm wide; argenteous, farinose abaxial; and glabrate adaxial; attenuate base; narrowly acute apex; no foliar fragrance detected;

*Leaf blade size*.—Up to about 16.2 cm long and about 3.7 cm wide, average about 12.5 cm long and about 2.8 cm wide; becoming smaller in distal portion of stem.

*Foliage color*.—Young expanding leaf adaxial nearest RHS 138A, young expanding abaxial nearest RHS 192A; mature leaves adaxial nearest and RHS NN137B, mature abaxial nearest RHS 191A.

*Veins*.—Reticulate; abaxial costate and farinose; adaxial glabrous, slightly impressed.

*Vein color*.—Adaxial midrib nearest RHS 160C, secondary veins nearest RHS NN137B, abaxial midrib between RHS 146D and RHS 145A, secondary veins nearest RHS 146D.

*Petioles*.—Short; farinose; concavo-convex; to about 4.0 mm long and 2.0 mm wide.

*Petiole color*.—Adaxial nearest RHS 191C; abaxial nearest RHS 194B.

*Inflorescence description*.—Glomerate thyrse consisting of up to about 5,000 self-cleaning salverform flowers, average about 3,700 flowers per inflorescence; to about 50 cm long and 17 cm wide at base; average about 44 cm long and 14.5 cm wide; beginning in mid-July and continuing until frost in Michigan; thyrse effective for about three weeks.

*Inflorescence attitude*.—Outwardly and drooping.

*Flower buds*.—Elongated clavate, apex rounded; one day prior to opening about 13.0 mm long, about 3.0 mm diameter in club, tube about 1.0 mm diameter and about 9.5 mm long.

*Flower bud color*.—Nearest RHS N87D in club portion, tube base nearest RHS NN155B, mid-section nearest RHS 185D and distal one-third nearest RHS 182D.

*Calyx*.—Campanulate; 3.0 mm long and 1.0 mm diameter at apex.

*Sepals*.—Typically four; adpressed to corolla tube; acute apex; glabrous adaxial and micro-puberulent to farinose abaxial; margin entire; fused in about the basal 2.0 mm and split in about the terminal 1.0 mm, individually less than about 1.0 mm wide at point of fusion.

*Sepal color*.—Variable; adaxial and abaxial nearest RHS 138A and RHS 187A.

*Flowers*.—Salverform; actinomorphic; perfect; to about 12.0 mm long and 10.0 mm wide at face; with straight terete tube about 9.0 mm long and 1.0 mm diameter at base and 2.5 mm wide before face, and a abruptly applanate face about 10.0 mm across; attitude outward from thyrse center; remaining on the thyrse and effective for about five to seven days.

*Flowers fragrance*.—Pleasantly and distinctly sweet.

*Petals*.—Typically four; glabrous abaxial and on adaxial blades and tube, puberulent center abaxial tube; blade rounded with crenate margin; apex rounded; blade to about 4.0 mm across and about 4.0 mm long from throat to apex.

*Petal color*.—Upon opening adaxial face nearest RHS N80A, when fully open at maturity between RHS N8OB and RHS N80; abaxial face blade between RHS N81C and RHS N81D; adaxial tube upon opening distally near face nearest RHS 14B, base nearest RHS NN155B and center nearest 176D; adaxial tube fully open distally near face nearest RHS 25A, base nearest RHS NN155B and center nearest RHS N167B; just before dropping distally near face nearest RHS 25A, base nearest RHS NN155B and center nearest RHS N167B; abaxial tube upon opening distally between RHS 174D and RHS 179D, base nearest RHS 145D, center nearest RHS 184B; abaxial tube mature and just before dropping base nearest RHS 145D, distally between RHS 174D and RHS 179D, center nearest RHS 183B.

*Gynoecium*.—Pistil: one; about 4.0 mm long. Style: glabrous, glutinous, ellipsoidal; about 1.3 mm long and about 0.2 mm diameter; color nearest RHS 145D. Stigma: narrow ellipsoidal, minutely puberulent; about 0.4 mm in diameter and about 1.3 mm long; color nearest RHS 146D. Ovary: superior; ellipsoidal, rounded apex and base; about 0.5 mm across at base and 1.0 mm tall; distally tapering to style; color nearest RHS 145A.

*Androecium*.—Typically four; adnate to inner corolla tube. Filaments: adnate to inner corolla tube for about 6.0 mm; free in distal 0.5 mm long and less than 0.1 mm diameter; adnate to middle of adaxial corolla tube; color same as inner corolla where attached and free portion nearest RHS 85D. Anthers: typically four; ellipsoidal; introrse; about 1.0 mm long and 0.3 mm wide; color nearest RHS 18C. Pollen: globose, less than 0.1 mm long; color nearest RHS 18C.

*Pedicel*.—Short; farinose; about 2.0 mm long and about 0.3 mm diameter; color between RHS N187C and RHS N187D.

*Peduncle*.—Cylindrical to angular and lightly furrowed; farinose; flexible and strong; to about 48.0 cm long, and about 5.0 mm across at base below flowers.

*Peduncle color*.—Nearest R.H.S.

*Fruit*.—Not observed.

*Seed*.—Not observed despite favorable conditions; fecundity or sterility not completely assessed.

Disease resistance: Resistance has been noted to deer browsing. Other pest and disease resistance beyond that common to butterfly bush cultivars has not been observed. The plant grows best with plenty of moisture and adequate drainage, but is able to tolerate some drought when mature.

Hardiness at least from USDA zone 6 through 10 with some occasional stem dieback.

It is claimed:

1. A new cultivar of winter-hardy butterfly bush plant named *Buddleia* 'Lilac Cascade' as herein illustrated and described.

* * * * *